United States Patent [19]

Tuy

[11] Patent Number: 5,757,951
[45] Date of Patent: May 26, 1998

[54] CORRECTION OF OFF-FOCAL RADIATION

[75] Inventor: Heang K. Tuy, Chesterland, Ohio

[73] Assignee: Picker International, Inc., Highland Heights, Ohio

[21] Appl. No.: 359,608

[22] Filed: Dec. 20, 1994

[51] Int. Cl.⁶ .............................. G06K 9/00; A61B 6/03; G01N 23/083
[52] U.S. Cl. .............................. 382/131; 382/132; 378/4; 378/901
[58] Field of Search .................. 364/413.01, 413.2, 364/413.13, 413.14, 413.21, 413.26; 378/4.12, 14.21, 901; 382/131, 132, 211, 255, 260, 265, 276, 279, 128

[56] References Cited

U.S. PATENT DOCUMENTS

| | | | |
|---|---|---|---|
| 4,189,775 | 2/1980 | Inouye et al. | 364/414 |
| 4,602,348 | 7/1986 | Heat | 364/581 |
| 4,751,644 | 6/1988 | Koka et al. | 364/414 |
| 4,809,172 | 2/1989 | Hopkinson et al. | 364/413.16 |
| 5,128,864 | 7/1992 | Waggener et al. | 364/413.21 |
| 5,140,520 | 8/1992 | Matsumura | 364/413.21 |
| 5,229,934 | 7/1993 | Mattson et al. | 364/413.21 |
| 5,243,664 | 9/1993 | Tuy | 382/6 |
| 5,355,310 | 10/1994 | Brunner | 364/413.21 |
| 5,361,291 | 11/1994 | Toth et al. | 378/12 |
| 5,400,255 | 3/1995 | Hu | 364/413.19 |
| 5,473,655 | 12/1995 | Hu | 378/901 |
| 5,473,656 | 12/1995 | Hsieh et al. | 378/901 |

FOREIGN PATENT DOCUMENTS

| | | |
|---|---|---|
| 353299 A1 | 2/1990 | European Pat. Off. . |
| 471455 A3 | 2/1992 | European Pat. Off. . |
| WO 87/02821 | 5/1987 | WIPO . |

Primary Examiner—Leo Boudreau
Assistant Examiner—Bhavesh Mehta
Attorney, Agent, or Firm—Fay, Sharpe, Beall, Fagan, Minnich & McKee

[57] ABSTRACT

An x-ray tube of CT or other radiographic scanner has a focal spot (30) from which x-rays with an energy distribution (32) are generated. As the x-ray source rotates a peak (34), the radiation energy distribution seen by each detector (24) through a physical collimator shifts. Each line of data generated by the detectors has a shifting energy distribution across its data values which creates artifacts in reconstructed images. A filter (50) includes a convolver (52) which convolves the lines of data with deconvolution functions from a memory (54) in a recursive loop (56) in accordance with a relative angular position of the x-ray tube and the corresponding detector. Filtered data lines are subtracted (56) from unconvolved data values to generate values with reduced off-focal radiation components. Filtered data is conveyed to a convolver (82) and a backprojector (84) which backprojects the data across an image memory (86).

17 Claims, 3 Drawing Sheets

CORRECTION OF OFF-FOCAL RADIATION

BACKGROUND OF THE INVENTION

The present invention relates to the art of diagnostic imaging. It finds particular application in conjunction with volume imaging with CT scanners and will be described with particular reference thereto. However, it is to be appreciated that the invention will also find application in conjunction with other types of x-ray imaging of human patients for medical diagnostic purposes, of manufactured articles to detect internal structures or flaws, and the like.

In CT scanners, a fan-shaped plane of radiation about 1 to 10 mm thick is projected through the subject and detected by a plurality of detectors. The output of the detectors is reconstructed into cross-sectional images of a subject representing a series of adjacent planes about 1 to 10 mm thick or a volume with 1 to 10 mm resolution.

In third and fourth generation CT scanners, an x-ray source produces radiation as the x-ray source rotates around the examination region. In a third generation scanner, the radiated detectors are rotated with the x-ray source and repeatedly sampled. In a fourth generation scanner, the examination region is surrounded by a stationary ring of detectors that are repeatedly sampled as the x-ray source rotates. The sampled data are then assembled in fans or views of data which are reconstructed, typically convolved and backprojected, to form a cross-sectional representation of the patient for display on a monitor.

Prior art methods of reconstructing CT images assume that data inputted to convolvers and backprojectors are in the form of line integrals. The line integrals are each an integral of the attenuation of radiation of a characteristic uniform intensity along a line between the detector and the focal spot of the x-ray source. The line integrals are estimated from data sampled from the plurality of the detectors. Unfortunately, sampled data from conventional CT scanner does not yield proportional line integrals. The x-ray radiation emanating from the x-ray source is in the form of a bundle of rays having differing strengths rather than a single ray of uniform intensity.

Rays from x-ray source are classified in two distinct groups. Rays from the center of the focal spot or on-focal radiation have a strong intensity and narrow base. Rays from regions of the anode surround the focal spot or off-focal radiation have a lower intensity but a broader base. Errors to line integral proportionality are introduced by the off-focal rays, i.e., those rays with a weak intensity origination over the broad base. The intensity errors and the broadened focal spot result in reconstructed images having major artifacts.

Prior art CT scanners have attempted to correct the adverse effects created by off-focal radiation with physical collimation and electronic notch filters. In particular, these CT scanners have attempted to incorporate a correction factor in the reconstruction filter, known as an image algorithm. This correction involves convolving sampled data with a constant kernel using a fast fourier transformer.

The prior art presumes that the off-focal radiation is static, i.e., the convolution kernel is invariant. The distribution of off-focal radiation as seen by the detector varies as a function of x-ray source position around the examination region. For instance, the detector at the center of a fan beam of radiation may see an intensity distribution having a large amplitude on-focal spike at the center with low amplitude off-focal shoulders to either side. As the x-ray source rotates, the detector may then see a large intensity on-focal spike at one side with an off-focal shoulder extending to the other side. Given the dynamic nature of the intensity distribution, convolving off-focal radiation using a constant deconvolution kernel will reduce off-focal effects for only a limited number of x-ray source positions, i.e. those positions which generate intensity distribution with on-focal spikes at the center.

The present application contemplates a new and improved CT scanner which overcomes the above referenced problems and others.

SUMMARY OF THE INVENTION

In accordance with the present invention, an apparatus and method are provided for filtering CT scanner data with x-ray source position dependent off-focal radiation filtering.

In accordance with another aspect of the present invention, a CT scanner is provided. A plurality of detectors are positioned to detect radiation from the x-ray source which has traversed a portion of a subject in an examination region. A data filter reduces x-ray source position dependent components from the sampled data by convolving the data with a deconvolution function or kernel defined as a function of the x-ray source position.

One advantage of the present invention is that it provides images having greater diagnostic valve.

Another advantage of the present invention is that it reduces artifacts from displayed images.

Yet another advantage of the present invention is that it removes x-ray source position dependent off-focal radiation components from the data collected from the detectors.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
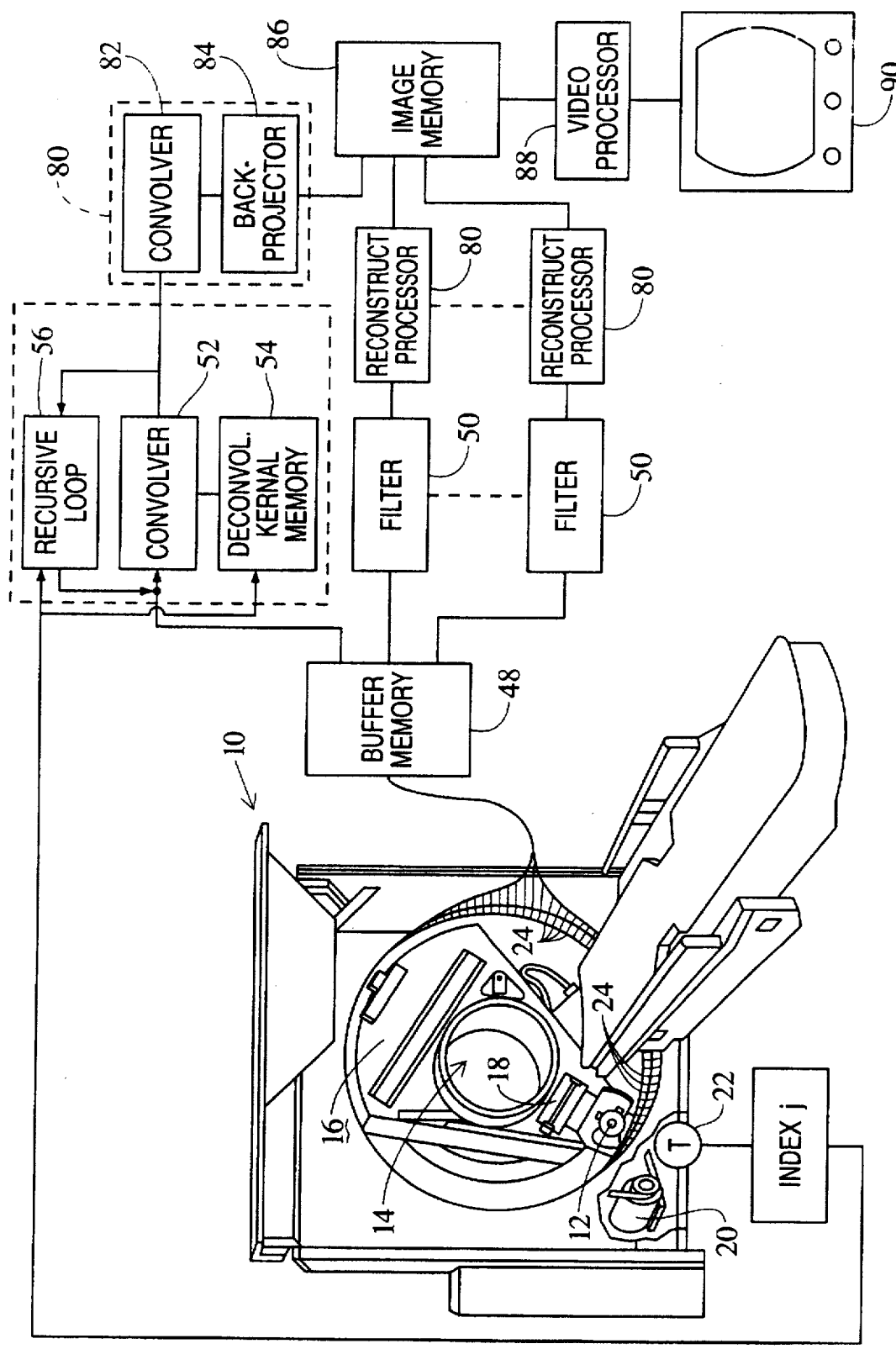
FIG. 1 is a diagrammatic illustration of a CT scanner in accordance with the present invention.

With reference to FIG. 1, CT scanner 10 includes a radiation source 12, such as an x-ray tube, for projecting a beam of radiation through an examination region or scan circle 14. The x-ray source 12 tube is mounted on a rotatable gantry 16 to rotate the fan beam of radiation around the examination region. A collimator and shutter 18 collimates the beam of radiation into one or more narrow fans and selectively gates the beam on and off. A motor 20 provides motive power for rotating the gantry 16, preferably continuously, around the examination region. A rotational position encoder or tachometer 22 is connected with the motor and gantry to measure the angular position or relative angle of the gantry and hence an apex of the fan beam of radiation.

In the illustrated fourth generation CT scanner, a ring of radiation detectors 24, preferably about 4,000 detectors, are mounted peripherally around the examination region. For mechanical and mathematical conveniences, the detectors 24 are stationarily mounted around the rotating gantry in the same plane as the x-ray tube. Alternately, an arc of detectors can be mounted to the rotatable gantry 16 across the examination region from the x-ray source, i.e. a third generation scanner.

Each of the radiation detectors produces an output signal proportional to an intensity of radiation having traversed the examination region 14. An optional reference detector (not shown) may detect radiation which has not traversed the subject in the examination region 14. A difference between the magnitude of the radiation received by the reference detector and each detector of the ring provides an indication of the amount of radiation attenuation along a corresponding ray of a sampled fan of radiation.

Figure 2:
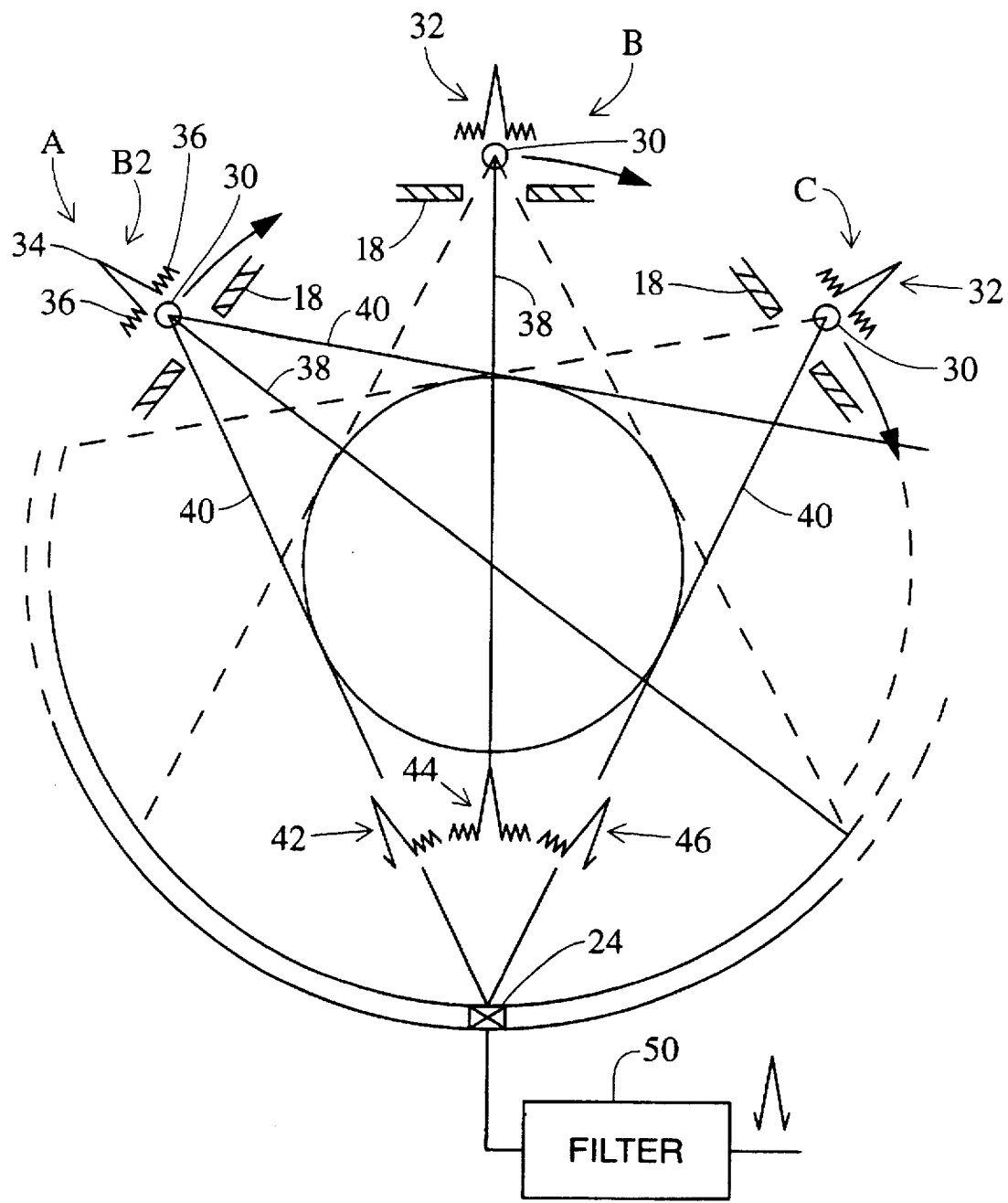
FIG. 2 is a diagrammatic illustration depicting the energy distribution offset problem and its correction.

With reference to FIG. 2, the x-ray tube 12 has a focal length 30, across which there is an energy distribution 32. The energy distribution includes a peak 34 of higher intensity radiation and shoulders 36 of lower intensity radiation. The collimator 18 defines an aperture such that a central ray 38 from the center of the focal spot traverses the center of the examination region 14. The edges of the collimator aperture limit the radiation to a fan with edge rays 40 that are tangent to opposite sides of the examination region.

An exemplary one of the radiation detectors 24 receives radiation as the x-ray source moves in back of the examination region. That is, the detector first sees the radiation source when it rotates to position A in which a leading edge tangential ray strikes the detector. In position A, parallax between the collimator 18 and the focal spot 30 causes the energy peak 34 to be offset as shown in distribution 42. As the x-ray source continues to rotate, the energy peak shifts. In x-ray source position B, in which the detector receives the central ray 38, the energy peak 34 is centered as shown in distribution 44. The peak continues to shift until as shown in position C only the trailing edge tangential ray strikes the detector. In the trailing edge detector ray, the energy peak 34 is shifted to a right side of the visible window as shown in distribution 46.

The detector, like the other detectors, is sampled repeated as the x-ray source rotates between positions A and C to generate the data values of a detector fan data line or view. It will be noted that the energy peak shifts with each point in the data line. Analogously, all detectors that are irradiated at one time by the fan of radiation can be sampled concurrently to generate data values of a source fan data line or view. Again, the position of the peak and the viewable portion of the energy distribution shift across the view. Of course, from the angular position of the focal spot as determined by the relative angular position encode 22 and the detector as determined by the geometry of the system, the shift in the energy distribution for each data value of a corresponding line is known. Due to the circular symmetry, the shift in the energy distribution for all like sampled data lines. In a third generation scanner, the energy distribution is the same for all source fan data lines. In a fourth generation scanner, if the detectors are sampled M times before the leading (or trailing) ray moves a distance or angle equal to one detector, there are M energy distribution shift patterns.

With reference to FIG. 1, the data lines are temporally stored and accumulated in a buffer memory 48 with an indication of its corresponding angular position around the examination region 14.

As each line of digital data is completed, it is filtered by filter 50 to reduce effects of x-ray source position dependent off-focal radiation. It will be noted that in fourth generation scanners, as the x-ray source moves, each irradiated detector is concurrently generating intensity data. In order to accommodate this rapid flow of information, the filter preferably includes a plurality of parallel filters to process several data lines concurrently.

Data d from the detectors can mathematically be represented by:

$$d = (\sigma + e) * X, \tag{1}$$

where X represents desired on-focal data from the distribution peak 34 along a ray from the x-ray source 12, and $e*X$ represents the error component sought to be filtered. The goal is to estimate X from the measured data d. From a theoretical point of view, X can be computed by convolving the data d with an estimated deconvolution function inversely related to ($\sigma+e$). Calculating X can be generally achieved using the following equation:

$$p_j = 2d_j - \Sigma k_i d_{j+i}, \tag{2}$$

where $k_i$ is an estimated deconvolution function whose values are dependent on x-ray source position and $p_j$ is related to X. The filter 50 implements Equation (2).

In the preferred embodiment, each filter 50 includes a convolver 52 which convolves data d from a line of data with deconvolution function retrieved from a deconvolution function memory 54. The deconvolution function memory 54 holds a plurality of estimated deconvolution functions for a plurality of x-ray source positions. The filter selects an appropriate deconvolution function in accordance with the relative angular position of the x-ray source and the detector for each data value of each data line to be convolved. A recursive loop 56 reduces the number of operations to produce $p_j$, as is more fully explained below.

The output of the filter 50 represents an approximation of X, the on-focal data. Error deviation for X is on the order of $x*e^2$ (power in convolution). A higher order of approximation can be mathematically derived. Second and third order corrections are provided as follows:

$$X \cong Y_2 - 3Y_1 + 3Y_0, \tag{3}$$

$$X \cong -Y_3 + 4Y_2 - 6Y_1 + 4Y_0, \tag{4}$$

where $Y_0 = d$, and $Y_{k+1} = (\delta + e) * Y_k$, for $k \geq 0$.

Radiation from the x-ray radiation source 12 can be described as a large amplitude spike at the center with low amplitude shoulders to either side as illustrated by distribution 32. At least, this is the distribution which the detector at the center of the fan beam sees. At one extreme of the fan, the radiation detector sees the spike offset completely to one side and a larger shoulder extending to the other side; at the other extreme ray of the fan, the spike is offset to the opposite side with the shoulder extending to the first side. The ray intensity from the x-ray radiation source is defined by:

$$f(i) = w_i \text{ if } |i| \leq N, \tag{5}$$

$$f(i) = w \text{ if } |i| > N, \tag{6}$$

where N is a fixed number, e.g. N=10. These predefined ray intensities f(i) provide the deconvolution functions in accordance with the following equation:

$$k_{ij} = \frac{f(i)}{\Sigma f(m)} \quad (7)$$

Normally, the right side denominator of the immediately preceding equation varies as a function of the scanner geometry and beam limiters of the x-ray source. However, with certain CT scanner equipment the summation of f(m) is independent of scanner geometries and beam limiters. CT scanners manufactured by Picker International Inc. of Highland Heights, Ohio exhibit these input characteristics. Using Picker CT scanners, the summation of f(m) can be replaced by a constant k. Accordingly, the deconvolution function is reduced to:

$$k_i = \frac{f(i)}{k} \quad (8)$$

Filtering off-focal radiation can also be implemented utilizing the equation as follows:

$$p_j = \Sigma q_i d_{i+j} \quad (9)$$

where q is a deconvolution function and is defined by:

$$q_0 = 2 - \frac{f(0)}{k} \quad (10)$$

and $$q_i = -\frac{f(i)}{k} \quad (11)$$

for $i \neq 0$.

The deconvolution memory has at least enough memory for storing 2N+2 values for deconvolution kernel q.

Looking at the present filtering technique from a more mathematical perspective, the final result for each ray j of a detector fan can be expressed by:

$$p_j = I_1 + Q(I_2 + I_3), \quad (12)$$

where the precomputed value Q is given by:

$$Q = -\frac{w}{k}, \quad (13)$$

and $I_1, I_2$ and $I_3$ can be expressed with the following:

$$I_1 = \Sigma q_i d_{j+i}, \quad (14)$$

for i=−N to i=N, and $$I_2 = \Sigma d_{j+i} \quad (15)$$

for j=S to j=−N−1 and j=n+1 to j=E, and $$I_3 = d_{j+S} + S(d_{j+S-1} - d_{j+S}) + d_{j+E} + e(d_{j+E+1} - d_{j+E}). \quad (16)$$

Before the final result for ray j are computed, the starting and end limits s(j) and e(j) respectively, are calculated using:

$$s(j) = a*j + b, \quad (17)$$

and $$e(j) = c*j + d \quad (18)$$

Moreover, the computational limits for s and e are calculated by taking the fixed value of s(j) and e(j). In other words, $$=S-s(j), \quad (19)$$

$$e = e(j) - E, \quad (20)$$

$$S = \text{fix}(s(j)), \quad (21)$$

and $$E = \text{fix}(e(j)). \quad (22)$$

In implementing the filtering equation set forth in equation 12, the kernel q(i) is restricted to a constant Q for all i different than zero. This is the case when N=0, but this condition does not impose any practical restriction since in practice, N is smaller than |s(0)| and |e(1023)| wherein ray 0 and ray 1023 are the first and last rays of each view, respectively. Consequently, the deconvolution kernel Q from −N to N is ray independent. Assuming N=0, the deconvolution formula of equation 12 can be rearranged to become:

$$P_j = (q(0) - Q)d_j + Q \Sigma d_{j+i}. \quad (23)$$

Consequently, the following recursive formula can be implemented by the recursive loop 56. In this formula, each ray $P_{j+1}$ is corrected based on the preceding ray $p_j$.

$$P_{j+1} = P_j + (q(o) - Q)(d_{j+1} - d_j) + Q*(A - S), \quad (24)$$

where A and S are calculated from the following expressions:

$$S = \Sigma d_k, \quad (25)$$

for k=j+s(j) to j+1+s(j+1), and $$A = \Sigma d_k, \quad (26)$$

for k=j+s(j) to j+1+e(j+1).

It should be noted that:

$$j+1+s(j+1) = (j+s(j)) + (1+a), \quad (27)$$

and $$j+1+e(j+1) = (j+e(j)) + (1+c). \quad (28)$$

A and S are computed by:

$$S = (1+a)d_{[j+s(j)]} + FP(j+1+s(j+1))(d_{[j+1+s(j+1)]} - d_{[j+s(j)]}), \quad (29)$$

and $$A = (1.30\ c)d_{[j+e(j)]} + FP(j+1+e(j+1))(d_{[j+1+e(j+1)]} - d_{[j+e(j)]}), \quad (30)$$

where [x] denotes the greatest integer $\leq x$ and $FP(x) = x - [x]$.

Within each view, these recursive relations reduce the number of operations to find $p_j$. To implement the recursive relations, the initial values are set as:

$$j = [-b/(1+a)+1], \quad (31)$$

$$s = (1+a)j + b, \quad (32)$$

$$m = [s], \quad (33)$$

$$fs = s - m, \quad (34)$$

$$e = (1+c)j + d, \quad (35)$$

$$n = [e], \quad (36)$$

$$fe = e - n, \quad (37)$$

and $$p_j = (q(0) - Q)^* d_j + Q^* (-fs^* d_m + d_{m+1} + \ldots + d_{n-1} + fe^* d_n). \quad (38)$$

In each iteration of the recursive loop 56, the variables are indexed as follows:

$$d0 = d_m, \quad (39a)$$

$$d1 = d_n, \quad (39b)$$

$$d = d_j, \quad (39c)$$

$$P = P_j, \quad (40)$$

$$s = s + (1+a), \quad (41)$$

$$m = \lfloor S \rfloor, \quad (42)$$

$$fs = s - m, \quad (43)$$

$$e = e + (1+c), \quad (44)$$

$$n = \lfloor e \rfloor, \quad (45)$$

$$fe = e - n, \quad (46)$$

$$j = j + 1, \quad (47)$$

and $$p_j = p + (q(0) - Q)^* (d_j - d) + Q^* ((1+c)^* d1 + fe^* (d_n - d1) - (1+a)^* d0 - fs^* (d_m - d0)). \quad (48)$$

The loop repeats until n reaches the last ray of the fan.

Figure 3:
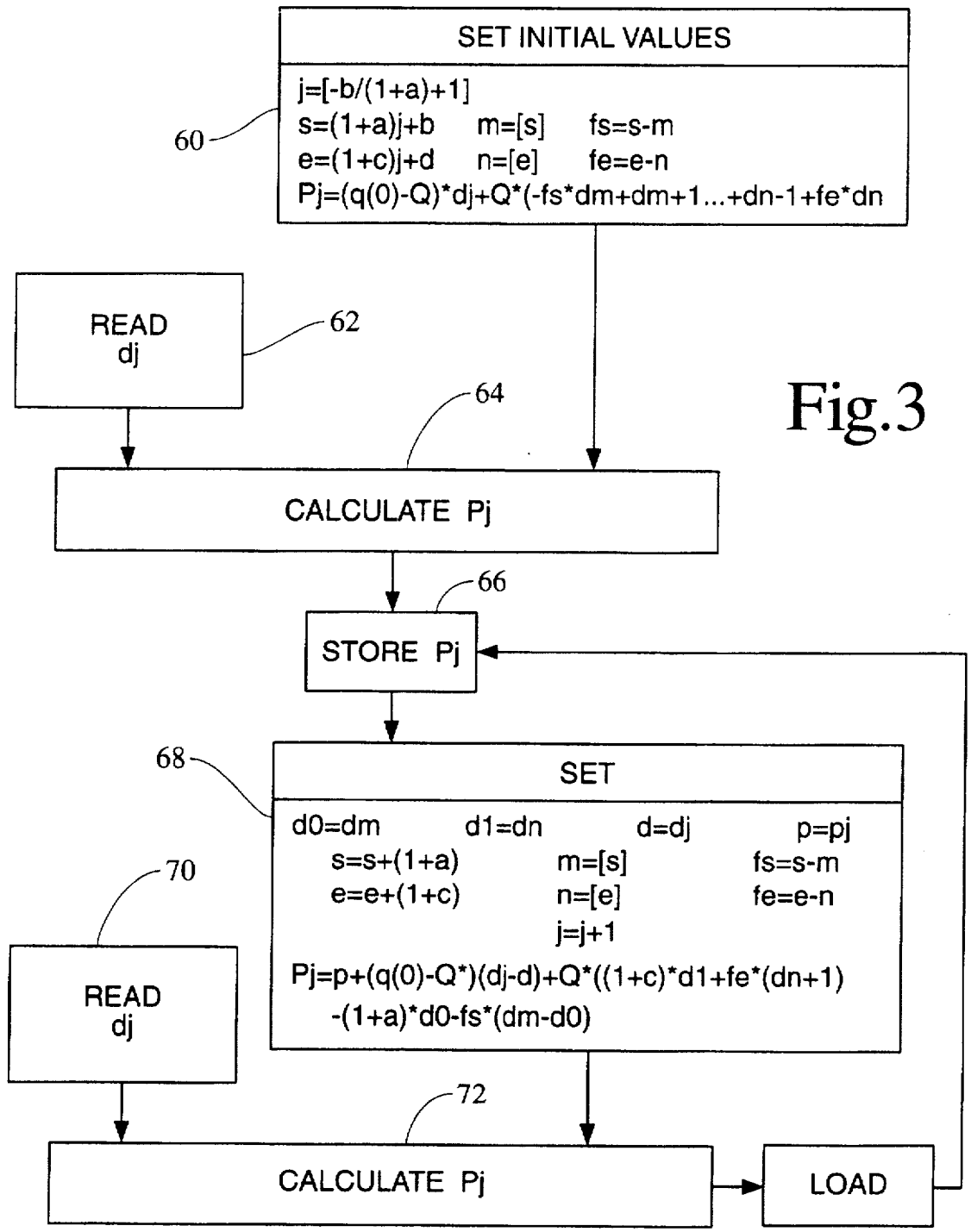
FIG. 3 is a flow chart diagramming data handling in the recursive loop of FIG. 1.

With reference to FIG. 3, the initial values of j, s, m, fs, e, n, fe, and $p_j$ are set in a step 60. The initial data value dj is read in a step 62. A processor or step 64 calculates $p_j$ in accordance with Equation 38. A memory 66 stores $p_j$. A step 68 resets the values according to Equations 39a–48 including indexes j. The next data value $d_j$ is read at step 70. The next value of $p_j$ is calculated at step 72 and loaded into the memory 66. The loop is iteratively repeated for all $d_j$.

After each line of data is filtered, it is conveyed to a reconstruction processor 80. In the preferred embodiment, the reconstruction processor includes a convolver 82 which convolves each filtered data line with a convolution or filter function. Again, to accommodate the rapid flow of information in fourth generation scanners, the convolver preferably includes parallel convolvers for convolving several filtered data lines concurrently. The convolved data lines are conveyed to a backprojector 84 which backprojects each convolved data line across an image memory 86 to reconstruct an electronic image representation.

A video processor 88 retrieves selected portions of the data in the image memory 86 and converts them to appropriate format for display on a video monitor 90. Exemplary images include single slice images, multiple slice images, surfaced rendered volume images, surface rendered volume images with cut planes, and the like. Reconstructed electronic images may also be sent to a central storage system for subsequent recall and viewing. Hard copy printers (not shown) convert the electronic images to human readable paper images.

The invention has been described with reference to the preferred embodiment. Obviously, modifications and moderations will occur to others upon reading and understanding the preceding detailed description. It is intended that the invention be construed as including all such modifications and alterations as far as they come in the scope and spirit of the appended claims or the equivalents thereof.

Having thus described the preferred embodiment, the invention is now claimed to be:

1. In a CT scanner which includes a radiation source which generates a beam of radiation, a cantry on which the radiation source is mounted for rotation around an examination region, a multiplicity of radiation detectors which receive radiation from the source that has traversed the examination region and convert the received radiation into electronic data, the improvement comprising:

an off-focal radiation filter which corrects the electronic data for off-focal radiation with a filter function that is dependent on a relative position of the radiation source and each radiation detector as each radiation detector converts the received radiation into a datum element of the electronic data, the off-focal radiation filter including:

a deconvolution memory for storing deconvolution functions, the deconvolution function memory being addressed in accordance with relative positions of the radiation source and the detectors to retrieve corresponding deconvolution functions; and a convolver for convolving the electronic data with the retrieved deconvolution functions.

2. In the CT scanner of claim 1, the improvement further comprising:

the convolver includes an iterative loop.

3. A CT scanner comprising:

an x-ray source for generating a fan beam of radiation which is directed across an examination region;

a rotatable gantry upon which the x-ray source is mounted for rotational movement;

an angular position encoder connected to the gantry for measuring a position of the x-ray source around the examination region;

detectors disposed across the examination region from the x-ray source for converting rays of the fan beam of radiation which has traversed the examination region into electronic data;

a first memory for storing the electronic data in fans, each fan having a plurality of logarithmic data values with each data value corresponding to a fan beam ray;

an off-focal radiation filter for filtering with a linear mathematic operation the data value corresponding to each ray of the electronic data with a filter function;

a means for changing the filter function in accordance with a relative angular position of each ray within the fan;

a first convolver for convolving the filtered electronic data fans;

a backprojector for backprojecting the convolved electronic data fans into an image memory; and a video processor for converting image data from the image memory into appropriate format for display.

4. The CT scanner of claim 3 wherein the off focal radiation filter filters electronic data corresponding to a plurality of rays in parallel.

5. A CT scanner comprising:

an x-ray source for generating a fan beam of radiation which is directed across an examination region;

a rotatable gantry upon which the x-ray source is mounted for rotational movement;

an angular Position encoder connected to the gantry for measuring a position of the x-ray source around the examination region;

detectors disposed across the examination region from the x-ray source for converting rays of the fan beam of radiation which has traversed the examination region into electronic data;

a first memory for storing the electronic data in fans, each fan having a plurality of data values with each data value corresponding to a fan beam ray;

an off-focal radiation filter including a first convolver for convolving each data fan stored in the first memory with deconvolution functions in accordance with a relative angular position of the x-ray source and a one of the detectors corresponding to each data value;

a means for changing the deconvolution function in accordance with a relative angular position of each ray within the fan;

a second convolver for convolving the filtered electronic data fans;

a backprojector for backprojecting the convolved electronic data fans into an image memory; and a video processor for converting image data from the image memory into appropriate format for display.

6. The CT scanner of claim 5 wherein the off-focal radiation filter further includes a third memory for storing a plurality of deconvolution functions.

7. A CT scanner comprising:

an x-ray source for generating a fan beam of radiation which is directed across an examination region;

a rotatable gantry upon which the x-ray source is mounted for rotational movement;

an angular position encoder connected to the gantry for measuring a Dosition of the x-ray source around the examination region;

detectors disposed across the examination region from the x-ray source for converting rays of the fan beam of radiation which has traversed the examination region into electronic data;

a first memory for storing the electronic data in fans, each fan having a plurality of data values with each data value corresponding to a fan beam ray;

an off-focal radiation filter for filtering the data value corresponding to each ray of the electronic data with a filter function, the off-focal radiation filter including a recursive loop in which the data value corresponding to each ray is filtered using a data value of a corresponding preceding ray;

a means for changing the filter function in accordance with a relative angular position of each ray within the fan;

a first convolver of convolving the filtered electronic data fans;

a backprojector for backprojecting the convolved electronic data fans into an image memory; and a video processor for converting image data from the image memory into appropriate format for display.

8. A CT scanner comprising:

an x-ray source;

a rotatable gantry upon which the x-ray source is mounted for rotational movement around an examination region;

a ring of detectors encircling the examination region to detect radiation from the x-ray source which has traversed a portion of a subject in the examination region;

a first convolver for convolving lines of data;

a backprojector for backprojecting convolved data lines into an image memory;

a video processor for converting image data from the image memory into a human-readable display on a monitor; and a means for reducing image artifacts in the human-readable display relating to radiation source position dependent off-focal radiation.

9. The CT scanner of claim 8 wherein the means for reducing images artifacts further includes an off-focal radiation filter for removing radiation position dependent off focal radiation components from the data lines.

10. A CT scanner comprising:

an x-ray source;

a rotatable gantry upon which the x-rav source is mounted for rotational movement;

a plurality of detectors positioned to detect radiation from the x-ray source which has traversed a portion of a subject in an examination region;

a first convolver for convolving lines of data;

a backprolector for backprojecting convolved data lines into an image memory;

a video processor for converting image data from the image memory into a human-readable display on a monitor; and an off-focal radiation filter for removing radiation position dependent off-focal radiation components from the data lines, the off-focal radiation filter including a second convolver for convolving data lines with a radiation ray position dependent deconvolution function.

11. A CT scanner comprising:

an x-ray source for generating a fan of radiation;

an array of detectors, each detector receiving radiation from the x-ray source which has traversed an examination region along a corresponding ray, each detector being sampled at intervals to generate corresponding data values;

a data filter for deconvolvinq the data values in accordance with relative angular positions of each corresponding ray within the radiation fan when the detector was sampled;

a first convolver for convolving the deconvolved data;

a backprojector connected to the convolver which backprojects the convolved data; and an image memory connected with the backprojector to receive and store the backprojected data.

12. The CT scanner of claim 11 wherein the data filter includes a second convolver for convolving data with a first deconvolution function.

13. The CT scanner of claim 12 wherein the data filter includes a third convolver for convolving data with a second deconvolution function concurrently with convolution of the second convolver.

14. The CT scanner of claim 13 wherein the data filter further includes a means for generating the first and second deconvolution functions in accordance with relative x-ray source and detector positions.

15. The CT scanner of claim 12 wherein the data filter further includes a recursive loop in which the data value is filtered as a function of a preceding data value.

16. A method of generating a CT scanner image comprising the steps of:

directing a fan beam of radiation from a focal spot across an examination region from a plurality of angular orientations;

rotating the focal spot around the examination region;

detecting radiation which has traversed a slice of the examination region with a stationary ring of radiation detectors encircling the examination region;

repeatedly sampling each radiation detector to convert the detected radiation into electronic data values;

filtering each electronic data value in accordance with a relative angular orientation of the focal spot relative to a corresponding one of the radiation detectors, said relative angular orientation being within the slice of the examination region;

convolving the filtered electronic data values;

backprojecting the convolved filtered electronic data values into an electronic image representation.

17. A method of generating a CT scanner image comprising the steps of:

directing a fan beam of radiation from a focal spot across an examination region from a plurality of angular orientations;

detecting radiation which has traversed a slice of the examination region with an arc of radiation detectors;

repeatedly sampling each radiation detector to convert the detected radiation into electronic data values;

deconvolving the electronic data with an x-ray source and detector relative angular orientation dependent deconvolution function, said relative angular orientation being within the slice of the examination region;

reconstructing the deconvolved electronic data values into an electronic image representation.

* * * * *